July 22, 1958 S. B. HUTTON, JR Plant Pat. 1,733
CHRYSANTHEMUM PLANT
Filed Dec. 2, 1957
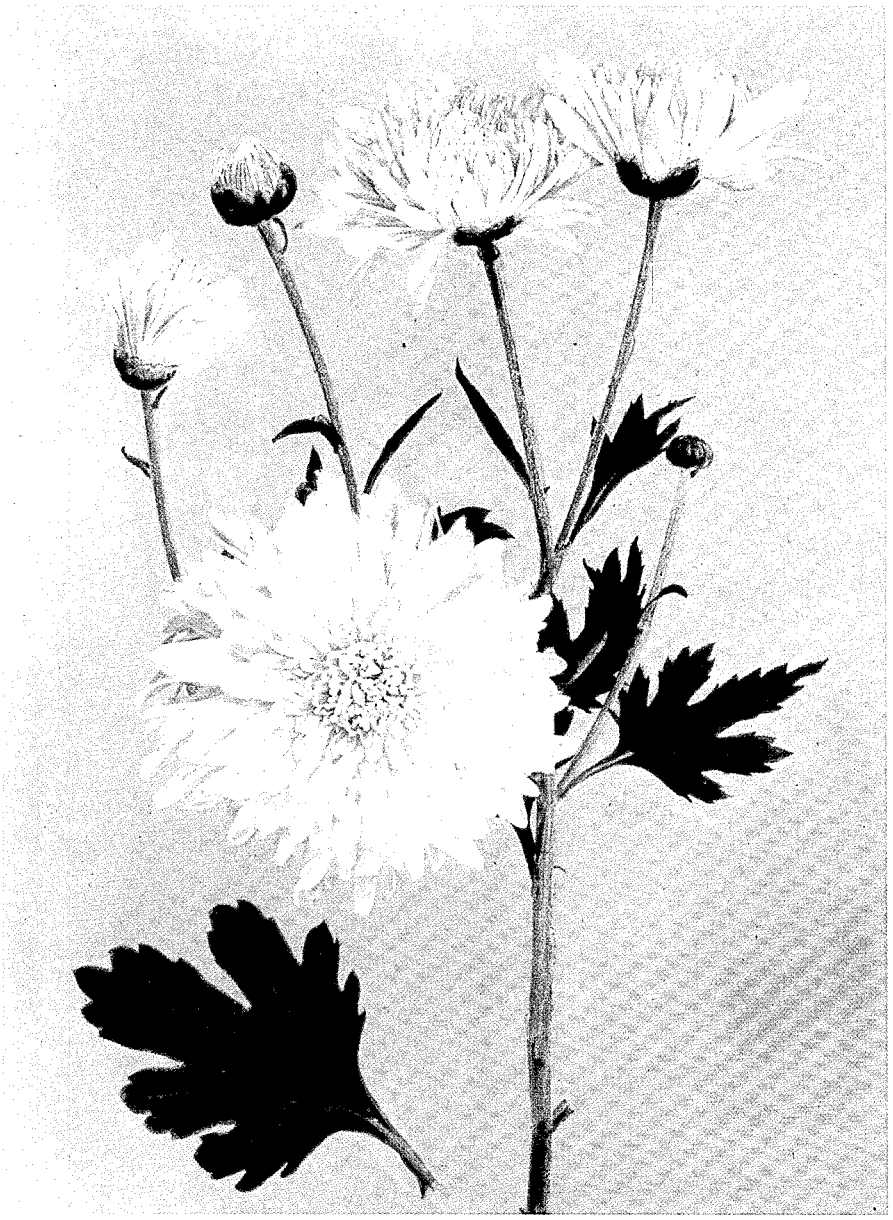
Inventor.
S. B. Hutton Jr.
By: Robert Cobb
Attorneys.

United States Patent Office

Plant Pat. 1,733

Patented July 22, 1958

1,733

CHRYSANTHEMUM PLANT

Sidney B. Hutton, Jr., West Grove, Pa., assignor to The Conard-Pyle Company, West Grove, Pa., a corporation of Pennsylvania Application December 2, 1957, Serial No. 700,243

1 Claim. (Cl. 47—60)

The present invention relates to a new and distinct variety of chrysanthemum plant of the decorative type, which was originated by me by crossing two unnamed and unpatented seedlings.

The primary objective of this breeding was to produce a new chrysanthemum variety which combines the typical compact habit of growth of one of the parent varieties with the typical large and well-formed flowers of the other parent variety. This objective was fully achieved, along with other improved features, as evidenced by the following characteristics which are outstanding in the new variety and which represent a unique combination in a chrysanthemum of this class:

(1) A compact and vigorous habit of growth;

(2) Large and well-formed blooms;

(3) A distinctive Canary Yellow general color tonality of the flowers;

(4) Adaptability to greenhouse pot forcing in the spring; and (5) Outstanding value for garden decoration.

The foregoing characteristics and distinctions definitely differentiate the new variety from its parents, as well as from all other varieties of its class of which I am aware, and asexual reproduction of the new variety by cuttings as performed at West Grove, Pennsylvania, shows that these characteristics and distinctions come true to form and are established and transmitted through succeeding propagations.

The accompanying drawing shows typical specimens of the vegetative growth and flowers of my new variety in different stages of development, and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious, as based upon observations made at West Grove, Pennsylvania:

Parentage: A cross of 2 unnamed seedlings.

Type: Hardy; medium height; outdoor; seedling; for greenhouse pot forcing and for garden decoration.

Classification:

*Horticultural.*—Decorative.

*Botanical.*—Hortorum.

Propagation: Holds its distinctive characteristics through succeeding propagations by cuttings.

*Flower*

Flowers borne: Several to stem; in irregular clusters; on strong stems of medium length.

Quantity of bloom: Abundant, outdoors.

Continuity: Continuous during September and October.

Fragrance: Moderate.

Bud:

*Peduncle.*—Medium length; medium caliper; erect; medium smoothness; with numerous hairs. Color—Lavender Green, Plate 000761/1.

*Before calyx breaks.*—Size—medium. Form—flat.

*As calyx breaks.*—Color—Canary Yellow, Plate 2.

*As petals open.*—Color: inside—Canary Yellow, Plate 2; outside—Barium Yellow, Plate 503.

*Opening.*—Opens up well.

Bloom:

*Size.*—About 4 inches.

*Form.*—Flat, with full center.

*Petalage.*—Fully double. Outer petals—straight; convex in transverse section. Inner petals—incurved; concave in transverse section.

*Color.*—Outer petals: inner surface—Canary Yellow, Plate 2; outer surface—Barium Yellow, Plate 503/2. Intermediate petals: inner surface—Canary Yellow, Plate 2/1; outer surface—Barium Yellow, Plate 503/1. Inner petals: inner surface—Canary Yellow, Plate 2; outer surface—Barium Yellow, Plate 503.

*General color effect of open bloom.*—Canary Yellow, Plate 2.

Ray flower petals: Thin; medium stiff.

*Inside.*—Velvety.

*Outside.*—Satiny.

*Size.*—Outer—long. Intermediate—medium length. Inner—short.

*Shape.*—Linear; no notches at apex.

Disk flower petals: Generally few; medium size; medium length; medium thickness. Color—Naples Yellow, Plate 403/3.

Flower longevity: On bush outdoors—10 days. Cut flowers grown outdoors and kept at living-room temperature—7 days.

*Genital organs*

Anthers: Few.

Stamens: Medium length.

Style: Medium length.

Stigma: Color—yellow.

*Plant*

Growth habit: Bushy; upright; much-branched; compact; attains height of about 18 inches and a spread of about 24 inches during the first year of growth.

Vigor: Vigorous.

Main stems: Color—Lavender Green, Plate 000761/1.

Branches: Color—Lavender Green, Plate 000761/1.

New growth: Color—Lavender Green, Plate 000761/1.

Foliage:

*Size.*—Medium.

*Texture.*—Thick; leathery.

*Upper surface.*—Rough; dull.

*Under surface.*—Rough; hirsute; dull.

*Quantity.*—Normal.

*Veins.*—Upper surface — prominent. Lower surface—prominent.

*Color.*—Young foliage: upper side—Spinach Green, Plate 0960; under side—midway between Willow Green, Plate 000862 and Willow Green, Plate 000862/1. Mature foliage: upper side—Parsley Green, Plate 00962; under side—Willow Green, Plate 000862.

I claim:

A new and distinct variety of chrysanthemum plant of the decorative type, substantially as herein shown and described, characterized particularly as to novelty by its compact and vigorous habit of growth, its large and well-formed blooms, the distinctive Canary Yellow general color tonality of its open blooms, and its suitability for greenhouse pot forcing in the spring, as well as its outstanding value for garden decoration.

No references cited.